US008675932B2

(12) United States Patent
Bernhardt et al.

(10) Patent No.: US 8,675,932 B2
(45) Date of Patent: Mar. 18, 2014

(54) METHOD FOR ESTABLISHING AT LEAST ONE CHANGE IN A TUBULAR TISSUE STRUCTURE IN A LIVING BEING, CALCULATION UNIT AND DATA STORAGE MEDIUM

(75) Inventors: Dominik Bernhardt, Hausen (DE); Christina Biermann, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 360 days.

(21) Appl. No.: 13/093,225

(22) Filed: Apr. 25, 2011

(65) Prior Publication Data
US 2011/0263964 A1 Oct. 27, 2011

(30) Foreign Application Priority Data
Apr. 27, 2010 (DE) .......................... 10 2010 018 460

(51) Int. Cl.
*G06K 9/00* (2006.01)
(52) U.S. Cl.
USPC ........................................................ 382/128
(58) Field of Classification Search
None
See application file for complete search history.

(56) References Cited

U.S. PATENT DOCUMENTS

| 7,356,367 | B2 | 4/2008 | Chen |
| 2008/0247621 | A1 | 10/2008 | Evron |
| 2009/0268954 | A1* | 10/2009 | Niinuma et al. ............. 382/128 |
| 2010/0061611 | A1 | 3/2010 | Bill |
| 2011/0103667 | A1 | 5/2011 | Biermann et al. |
| 2011/0235891 | A1* | 9/2011 | Sonnemans et al. ......... 382/133 |

FOREIGN PATENT DOCUMENTS

| DE | 102007028065 A1 | 1/2009 |
| DE | 102007045268 A1 | 4/2009 |
| DE | 102009006414 B3 | 9/2010 |
| DE | 102009032257 A1 | 1/2011 |
| DE | 102009052315 | 5/2011 |

OTHER PUBLICATIONS

Sharaf, Barry L., et al. "Detailed angiographic analysis of women with suspected ischemic chest pain (pilot phase data from the NHLBI-sponsored Women's Ischemia Syndrome Evaluation [WISE] Study Angiographic Core Laboratory)." The American journal of cardiology 87.8 (2001): 937-941.*

(Continued)

*Primary Examiner* — Nirav G Patel
(74) *Attorney, Agent, or Firm* — Harness, Dickey & Pierce, P.L.C.

(57) ABSTRACT

A method is disclosed for establishing at least one change in a tubular tissue structure in a living being from a first time to a second time, which differs from the first, wherein the midline of the tubular tissue structure is respectively determined in a provided first volume data record, generated at the first time, of the tubular tissue structure in the living being, and in a provided second volume data record, generated at the second time, which differs from the first, of the tubular tissue structure. In at least one embodiment, at least one change in the minimum and/or the maximum diameter of the inner wall of the tubular tissue structure and/or at least one change in the minimum and/or the maximum diameter of the outer wall of the tubular tissue structure is established in order to establish the at least one change in the tubular tissue structure along the tubular tissue structure at mutually corresponding positions of the midlines of the tubular tissue structure in the first volume data record and the tubular tissue structure in the second volume data record. At least one embodiment of the invention also relates to a calculation unit for carrying out the method and to a data storage medium, which has a calculation program implementing the method.

18 Claims, 5 Drawing Sheets

(56) References Cited

OTHER PUBLICATIONS

Yang, Chun, et al. "Advanced human carotid plaque progression correlates positively with flow shear stress using follow-up scan data: An *in vivo* MRI multi-patient 3D FSI study." Journal of biomechanics 43.13 (2010): 2530-2538.*

Lehman, Sam J., et al. "Assessment of coronary plaque progression in coronary computed tomography angiography using a semiquantitative score." JACC: Cardiovascular Imaging 2.11 (2009): 1262-1270.*

Brewster, D.C. et al., "Guidelines for the treatment of abdominal aortic aneurysms", American Association for Vascular Surgery, J.C. & for Vascular Surgery, S. (2003), Report of a subcommittee of the Joint Council of the American Association for Vascular Surgery and Society for Vascular Surgery, J Vasc Surg 37 (5), 1106-1117; Others; 2003.

Georgescu, B., et al., "Database-Guided Segmentation of Anatomical Structures with Complex Appearance", 'CVPR '05: Proceedings of the 2005 IEEE Computer Society Conf. on Computer Vision and Pattern Recognition (CVPR'05) - vol. 2', IEEE Comp. Soc., Washington, DC, USA, pp. 429-436; Others; 2005.

Zheng, Y. et al., "Four-Chamber Heart Modeling and Automatic Segmentation for 3D Cardiac CT Volumes Using Marginal Space Learning and Steerable Features", IEEE Trans. Medical Imaging (2008) 27 (11), pp. 1668-1681; Others; 2008.

German priority document DE 10 2010 018 460.8, filed Apr. 27, 2010, not yet published.

* cited by examiner

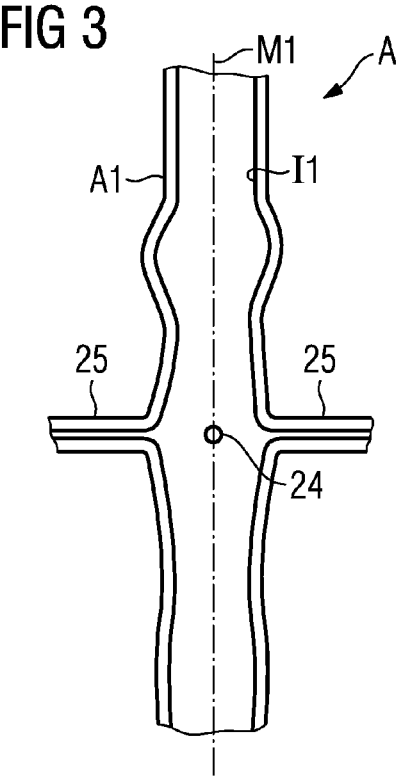
FIG 3
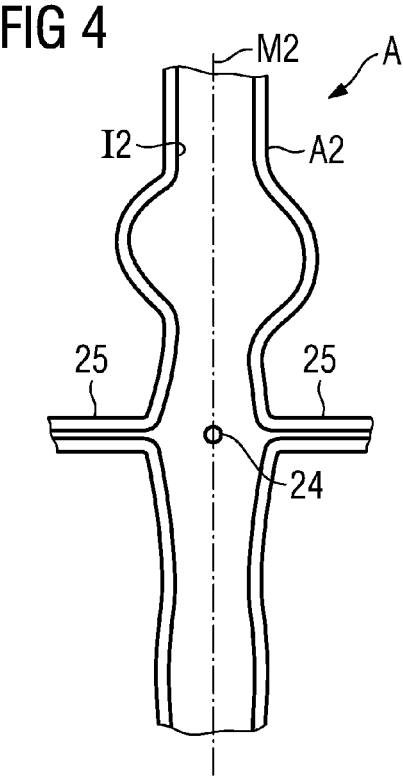
FIG 4
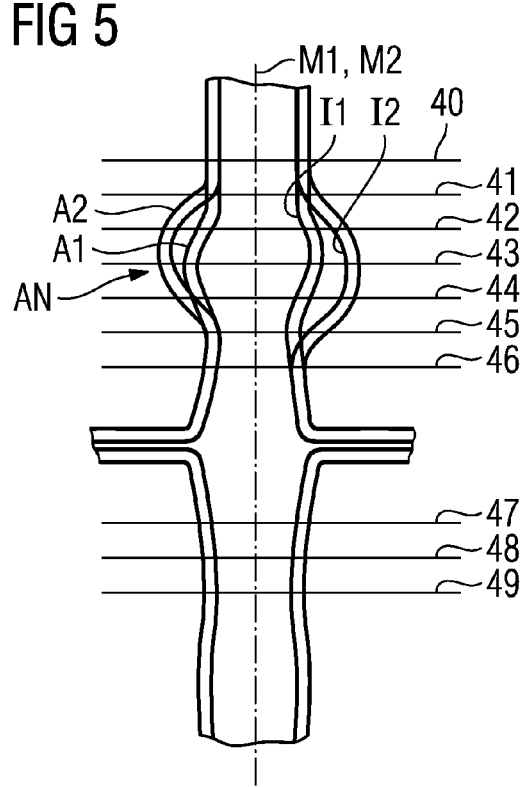
FIG 5
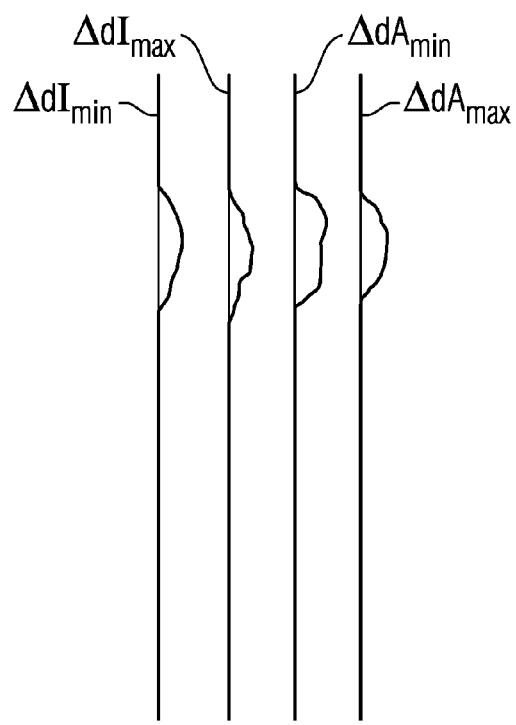

METHOD FOR ESTABLISHING AT LEAST ONE CHANGE IN A TUBULAR TISSUE STRUCTURE IN A LIVING BEING, CALCULATION UNIT AND DATA STORAGE MEDIUM

PRIORITY STATEMENT

The present application hereby claims priority under 35 U.S.C. §119 on German patent application number DE 10 2010 018 460.8 filed Apr. 27, 2010, the entire contents of which are hereby incorporated herein by reference.

FIELD

At least one embodiment of the invention generally relates to a method for establishing at least one change in a tubular tissue structure in a living being from a first time to a second time, which differs from the first. At least one embodiment of the invention moreover relates to a calculation unit for carrying out the method and to a data storage medium, which has a calculation program implementing at least one embodiment of the method.

BACKGROUND

Modern imaging instruments, such as computed tomography scanners or magnetic resonance imaging scanners, allow the generation of high-resolution images of the interior of a body of a human for examinations and for diagnostic purposes. The generation of such high-resolution images also extends to tubular tissue structures, for example blood-carrying vessels or vessel systems, in humans using e.g. CT angiography (CTA) under administration of a contrast agent in order to be able to identify anomalies, such as stenoses or aneurysms, in the vessels or the vessel system and monitor changes, more particularly increases in size, within the scope of a subsequent examination, which is so-called follow up examination.

Should an aneurysm be identified, the maximum diameter of the aneurysm is generally established and stored. During a follow up examination, carried out at a later date, the maximum diameter of the aneurysm is determined once again in order to establish the increase in the maximum diameter of the aneurysm. If the maximum diameter of the aneurysm increases by more than 1 cm within a year, it is suggested to treat the aneurysm by surgery (cf. Brewster, D. C.; Cronenwett, J. L.; Hallett, J. W.; Johnston, K. W.; Krupski, W. C.; Matsumura, "Guidelines for the treatment of abdominal aortic aneurysms", Report of a subcommittee of the Joint Council of the American Association for Vascular Surgery and Society for Vascular Surgery, Journal of Vascular Surgery, Volume 37, No. 5, 2003, pages 1106-1117).

The ever-improving image quality that can be obtained in modern imaging instruments goes hand in hand with an increasing number of images to be diagnosed. The upshot of this is that, for example, when images of blood-carrying vessels are diagnosed in respect of aneurysms, the effort required for viewing and evaluating the images is relatively high, particularly for determining the change in the maximum diameter of each aneurysm. Moreover, there is the risk of overlooking an aneurysm or measuring it incorrectly.

SUMMARY

In at least one embodiment of the invention a method, a calculation unit and/or a data storage medium is specified such that there is improved support for establishing a change in a tubular tissue structure in a living being.

According to at least one embodiment of the invention, a method is disclosed for establishing at least one change in a tubular tissue structure in a living being from a first time to a second time, which differs from the first, wherein the midline of the tubular tissue structure is respectively determined in a provided first volume data record, generated at the first time, with image data of the tubular tissue structure in the living being, and in a provided second volume data record, generated at the second time, which differs from the first, with image data of the tubular tissue structure. Various methods are available for establishing the midline of a tubular tissue structure. By way of example, use can be made of one of the methods described in the patent applications DE 10 2009 006 414.1 and DE 10 2009 032 257.4, which do not have a prior publication date and wherein the entirety of the disclosure of each of these documents is hereby incorporated herein by reference.

The inner wall of the tubular tissue structure and/or the outer wall of the tubular tissue structure is/are respectively determined or segmented in the first volume data record of the tubular tissue structure and in the second volume data record of said tubular tissue structure. To this end, e.g. learning-based methods can be utilized, applied to the present tubular tissue structure (cf. Georgescu, B.; Zhou, X. S.; Comaniciu, D. and Gupta, A. in "Database-Guided Segmentation of Anatomical Structures with Complex Appearance", in CVPR 05: Proceedings of the 2005 IEEE Computer Society Conference on Computer Vision and Pattern Recognition (CVPR 05)—Volume 2, IEEE Computer Society, Washington, D.C., USA, pp. 429-436, the entirety of the which is hereby incorporated herein by reference).

The tubular tissue structure in the first volume data record and the tubular tissue structure in the second volume data record are registered with respect to one another on the basis of their midlines, with, in particular, characteristic anatomical landmarks of the tubular tissue structure being used for this purpose.

After the registration, respectively the minimum and/or the maximum diameter of the inner wall of the tubular tissue structure and/or respectively the minimum and/or the maximum diameter of the outer wall of the tubular tissue structure is/are established along the midline of the tubular tissue structure in the first volume data record and along the midline of the tubular tissue structure in the second volume data record. The diameters are preferably established in corresponding cross-sectional planes of the tubular tissue structure in the first volume data record and the tubular tissue structure in the second volume data record, or the diameters are respectively established in one cross-sectional plane in the first and second volume data records, which are registered with respect to one another, wherein each cross-sectional plane is preferably aligned at a right angle to the respective midline.

In order to establish at least one change in the tubular tissue structure along the tubular tissue structure, at least one change in the minimum and/or the maximum diameter of the inner wall of the tubular tissue structure and/or at least one change in the minimum and/or the maximum diameter of the outer wall of said tubular tissue structure is preferably established at a plurality of mutually corresponding positions along the midlines and/or along the midlines in mutually corresponding cross-sectional planes of the tubular tissue structure in the first volume data record and the tubular tissue structure in the second volume data record and/or along the midline resulting from registration, respectively in one cross-sectional plane in the first and second volume data records, which are registered with respect to one another. The change is preferably established by forming the difference and/or quotient of mutually corresponding diameter values.

This provides the conditions for automated identification of changes in a tubular tissue structure in a living being, which changes have occurred from a first time, in particular during a first examination of the tubular tissue structure, to a second time, in particular during a second examination or a follow up examination of the tubular tissue structure.

According to one variant of at least one embodiment of the invention, the at least one change in the tubular tissue structure, which change occurred from the first to the second time, is visualized. It is preferable if all changes that occurred and are identified in the tubular tissue structure are visualized. Here, according to one embodiment of the invention, the at least one change in the minimum and/or the maximum diameter of the inner wall of the tubular tissue structure and/or in the minimum and/or the maximum diameter of the outer wall of the tubular tissue structure can be visualized. By way of example, such visualization could be brought about in the form of curve profiles, which are related to the midlines registered with respect to one another and/or to the midline of the tubular tissue structure resulting therefrom, which curve profiles respectively visualize the changes in the individual diameters along the midlines.

According to a further embodiment of the invention, the change in the cross-sectional area of the tubular tissue structure can be calculated and visualized on the basis of the established at least one change in the minimum and/or the maximum inner diameter and/or outer diameter of the tubular tissue structure in the cross-sectional plane of the tubular tissue structure belonging to the at least one change. In this case too, a curve profile could visualize the changes in the cross-sectional area of the tubular tissue structure along the midline of the tubular tissue structure, which curve profile is related to the midlines registered with respect to one another and/or to a resulting midline of the tubular tissue structure.

Another variant of at least one embodiment of the invention provides for at least one difference surface, relating to the outer wall of the tubular tissue structure and/or to the inner wall of the tubular tissue structure, and the outer contour and/or inner contour, which belong to the difference surface, are established on the basis of the established at least one change in the minimum and/or the maximum inner diameter and/or outer diameter of the tubular tissue structure in the cross-sectional plane of the tubular tissue structure belonging to the at least one change. Preferably, at least one difference surface, relating to the outer wall of the tubular tissue structure and/or to the inner wall of the tubular tissue structure, and the outer contour and/or inner contour of the respective difference surface are established for each cross-sectional plane comprising a change, with this being based on a plurality of established changes in the minimum and/or the maximum inner diameter and/or outer diameter of the tubular tissue structure in successive cross-sectional planes of the tubular tissue structure in the direction of the midlines, which cross-sectional planes belong to the changes.

According to a further variant of at least one embodiment of the invention, the outer contours of successive difference surfaces in the direction of the midlines, or the resulting midline, form an outer contour surface and the inner contours of successive difference surfaces in the direction of the midlines, or the resulting midline, form an inner contour surface, wherein a texture is imaged on the outer contour surface and/or the inner contour surface, which texture visualizes the degree of the change or the amount of change at various locations on the outer contour surface and/or the inner contour surface. Different degrees of the change are preferably visualized using different colors. Here the texture is virtually an image, which is imaged or mapped onto a contour surface, and different colors make differently pronounced changes in the tubular tissue structure visible without influencing the geometry of the change.

Once a region of the tubular tissue structure, in which the values of the inner wall and/or outer wall diameter of the tubular tissue structure have changed, has been identified and once a contour surface has been established, the contour surface can be superimposed onto the first and/or second volume data record of the tubular tissue structure and the texture can be imaged or mapped onto the contour surface for vivid visualization of the changes in the tubular tissue structure. By way of, example, small changes can be visualized in green, medium severe changes can be visualized in yellow and severe changes can be visualized in red in the respective region, wherein the colored designations may merge into one another. This immediately indicates the locations with a change in the tubular tissue structure. Moreover, this immediately indicates how the tubular tissue structure has changed at the identified locations.

According to one embodiment of the invention, the tubular tissue structure has at least one blood-carrying vessel, for example the aorta of a human. The tubular tissue structure preferably is a vessel system of blood-carrying vessels. Accordingly, the method according to at least one embodiment of the invention can be used to monitor and visualize the local changes or the local growth of aneurysms in the aorta.

At least one embodiment of the present invention is directed to a calculation unit, which is embodied in program-technical terms for carrying out one of the above-described methods.

At least one embodiment of the present invention is directed to a data storage medium, comprising a calculation program implementing one of the above-described methods. The calculation program is stored on the data storage medium and can be loaded from the data storage medium by a calculation unit in order to be carried out by the calculation unit. The data storage medium may be a portable data storage medium, e.g. a CD, or a server, etc.

BRIEF DESCRIPTION OF THE DRAWINGS

An example embodiment of the invention is illustrated in the attached schematic drawings, in which:

FIG. 3 shows a schematic illustration of the aorta of a patient, contained in a first volume data record, FIG. 4 shows a schematic illustration of the aorta of a patient, contained in a second volume data record, FIG. 5 shows the aortas, which have been registered with respect to one another, of the first and the second volume data record.

DETAILED DESCRIPTION OF THE EXAMPLE EMBODIMENTS

Figure 1:
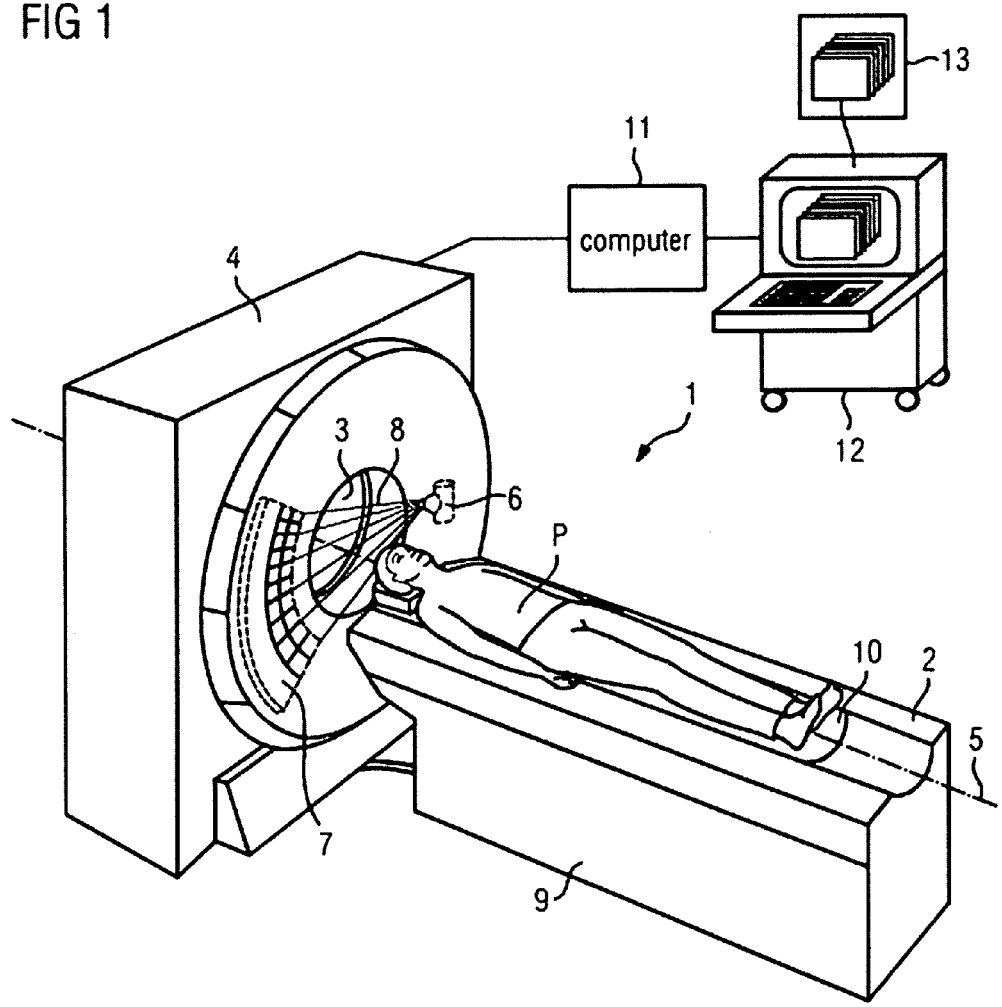
FIG. 1 shows a computed tomography scanner for examining a patient.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements, components, tissues, etc. are always denoted by the same reference sign. The illustrations in the figures are schematic and not necessarily true to scale, wherein the scale may vary between the figures. In the following text, and without loss of generality, the X-ray computed tomography scanner 1 illustrated in FIG. 1 is only addressed to the extent considered necessary for understanding the invention.

The X-ray computed tomography scanner 1 shown in figure has a patient couch 2 for supporting a patient P to be examined. The X-ray computed tomography scanner 1 furthermore comprises a gantry 4 with a tube-detector system mounted such that it can rotate about a system axis 5. The tube-detector system has an X-ray tube 6 and an X-ray detector unit 7 that mutually oppose one another. During operation, X-ray radiation 8 emanates from the X-ray tube 6 in the direction of the X-ray detector unit 7 and is registered by the latter.

The patient couch 2 has a couch base 9, on which there is arranged a patient support table 10 provided for actually supporting the patient P. The patient support table 10 can be adjusted relative to the couch base 9 such that the patient support table 10 with the patient P can be inserted into the opening 3 of the gantry 4 for the purpose of recording 2D X-ray projections of the patient P, for example in a helical scan. The computational processing of the 2D X-ray projections or the reconstruction of a volume data record of a body region of the patient P on the basis of the 2D X-ray projections is performed by a schematically illustrated image computer 11 of the X-ray computed tomography scanner 1.

In the case of the present example embodiment of the invention, a tubular tissue structure of the patient P is examined using the X-ray computed tomography scanner 1. Specifically, the aorta of the patient P is examined in the present case in respect of an aneurysm growth. To this end, two volume data records of the aorta of the patient P were generated by the X-ray computed tomography scanner 1, respectively after administration of a contrast agent, with approximately one year passing between the two examinations. The second volume data record is intended to be used to examine the growth of the aneurysm identified in the first volume data record generated approximately one year earlier.

In order to assist e.g. a diagnosing medical practitioner in an improved fashion during this examination, a calculation unit 12, which can for example be a diagnostic workstation, is provided with an appropriate calculation program 13, which in the present case was loaded into the calculation unit 12 by way of a portable storage medium, e.g. a CD, or from a server via a network and comprises program means for establishing at least one change in the aorta of the patient P.

The calculation unit 12 is connected to the image computer 11 of the X-ray computed tomography scanner 1, which image computer makes the first and the second volume data record of the aorta available to the calculation unit 12.

Figure 2:
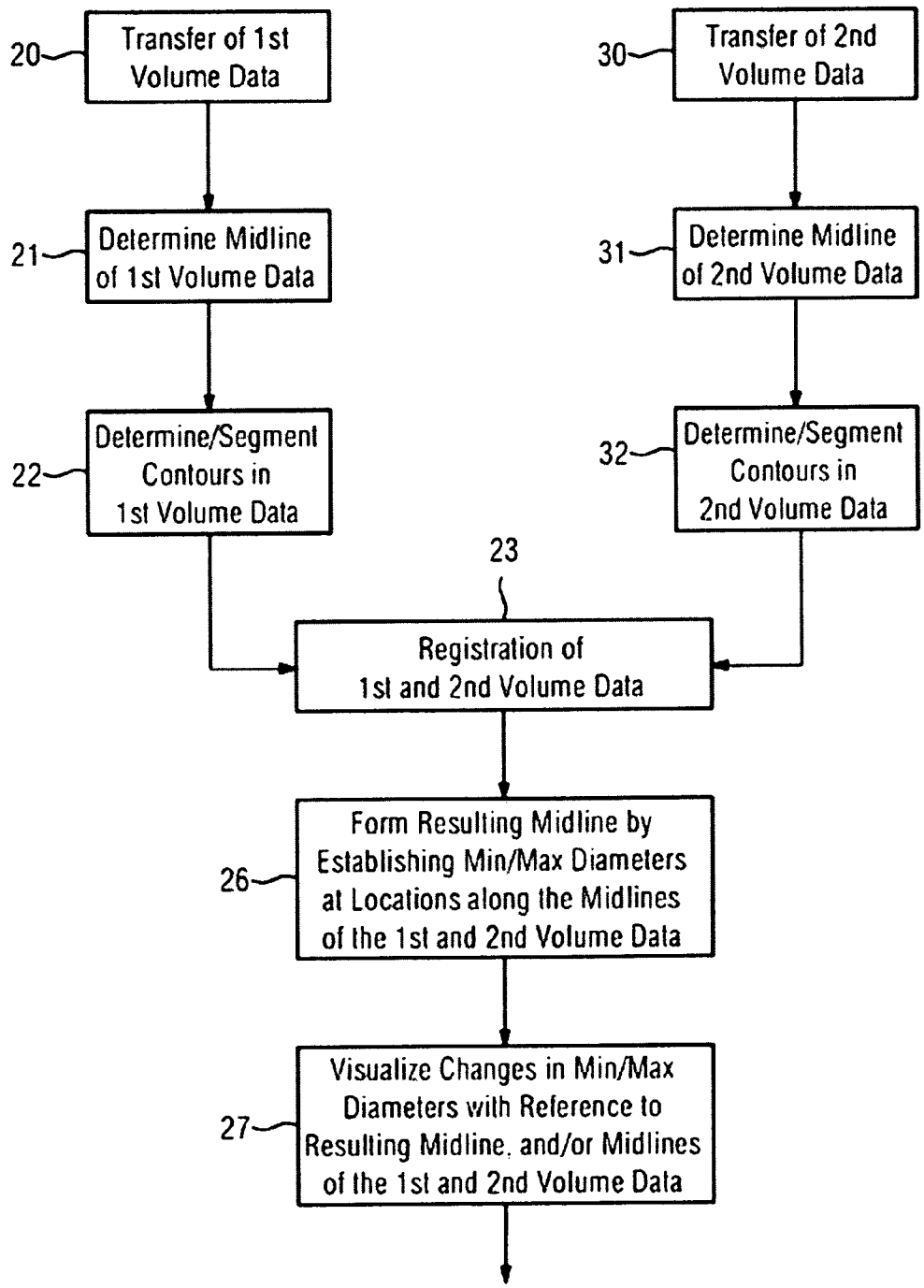
FIG. 2 shows a flowchart of the method according to an embodiment of the invention.

FIG. 2 visualizes the basic sequence of the method according to an embodiment of the invention. In step 20, the first volume data record of the aorta of the patient P, which was generated approximately one year earlier, is transferred from the image computer 11, or else from a data archive (not illustrated), to the calculation unit 12 and in step 30 the same transfer is carried out for the second volume data record of the aorta of the patient P, which was generated at the present time.

In step 21, the midline M1 of the aorta A is determined in the first volume data record of the aorta A of the patient P, which volume data record is illustrated schematically in FIG. 3. The midline M1 of the aorta A is preferably determined in a fully automated fashion on the basis of the image data in the first volume data record of the aorta A. To this end, use can for example be made of the methods already mentioned at the outset, which are described in the German patent applications DE 10 2009 006 414.1 or DE 10 2009 032 257.4 that do not have a prior publication date, the entire contents of each of which is, hereby incorporated herein by reference. Use can alternatively also be made of semi-automatic methods for determining the midline. However, this increases the amount of time required for establishing the midline. In step 31, the midline M2 of the aorta A is determined in a corresponding fashion in the second volume data record of the aorta A of the patient P, which volume data record is illustrated schematically in FIG. 4.

The contours of the vessel walls of the aorta are determined or segmented in step 22, more particularly the inner wall I1 and the outer wall A1 are segmented in the first volume data record of the aorta. To this end, use can be made of active contour models. However, active contour model algorithms may fail in the case of a blood vessel that comprises an aneurysm with atheromatous plaque deposits on the vessel wall, which is why learning-based methods such as the "Marginal Space Learning" are preferred, which, as already mentioned at the outset, was presented by Georgescu, B.; Zhou, X. S.; Comaniciu, D. and Gupta, A. in "Database-Guided Segmentation of Anatomical Structures with Complex Appearance", in CVPR 05: Proceedings of the 2005 IEEE Computer Society Conference on Computer Vision and Pattern Recognition (CVPR 05)—Volume 2, IEEE Computer Society, Washington, D.C., USA, pp. 429-436, the entire contents of which is hereby incorporated herein by reference and has already found first application in cardiac segmentation (cf. Zheng, Y.; Barbu, A.; Georgescu, B.; Scheuering, M. and Comaniciu, D. (2008), in "Four-chamber heart modeling and automatic segmentation for 3D cardiac CT volumes using marginal space learning and steerable features", IEEE Transactions on Medical Imaging 27(11), 1669-1681, the entire contents of which is hereby incorporated herein by reference). The inner wall I2 and the outer wall A2 in the second volume data record of the aorta A are segmented in a corresponding fashion in step 32.

In step 23, the aorta in the first volume data record and the aorta in the second volume data record are registered with one another or to one another on the basis of their midlines M1, M2. Registration preferably also uses anatomical landmarks. Thus, various branchings from the aorta may be used as anatomical landmarks. The location 24 in the aorta A level with the renal artery 25 branchings, plotted in FIG. 3 and FIG. 4, or the left and right common iliac artery branchings (not shown in the figures) are mentioned in an exemplary fashion. FIG. 5 visualizes the result of the registration. It can be identified from FIG. 5 that the inner wall I1 and the inner wall I2, and also the outer wall A1 and the outer wall A2, of the aorta A from both volume data records ideally overlap entirely in part. However, there are differences or deviations in the region of anomalies in the aorta. In the case of the present exemplary embodiment of the invention, there is such an anomaly in the form of the aneurysm AN, which has to be measured in order to be able to make a diagnosis.

In the case of the present example embodiment of the invention, once the aorta in the first volume data record and the aorta in the second volume data record have been registered to one another, respectively the minimum and the maximum diameter of the inner wall I1, I2 and respectively the minimum and the maximum diameter of the outer wall A1, A2 are, at least in sections, established in an automated fashion in step 26 at corresponding locations along the midline M1 of the aorta in the first volume data record and along the midline M2 of the aorta in the second volume data record, which midlines ideally overlap to form a resulting midline, as illustrated in the present case in FIG. 5. To this end, cross-sectional planes are placed through the aorta at corresponding locations along the midlines M1, M2, wherein a cross-sectional plane is arranged at a right angle to the respective midline M1, M2.

For the exemplary visualization of this procedure, corresponding cross-sectional planes 40 to 49 are plotted in FIG. 5 at corresponding locations in the aorta in the first volume data record and the aorta in the second volume data record. The number of cross-sectional planes should merely be understood as being exemplary; i.e. both more and also fewer dross-sectional planes may be placed through the aorta of the respective volume data record.

Figure 6:
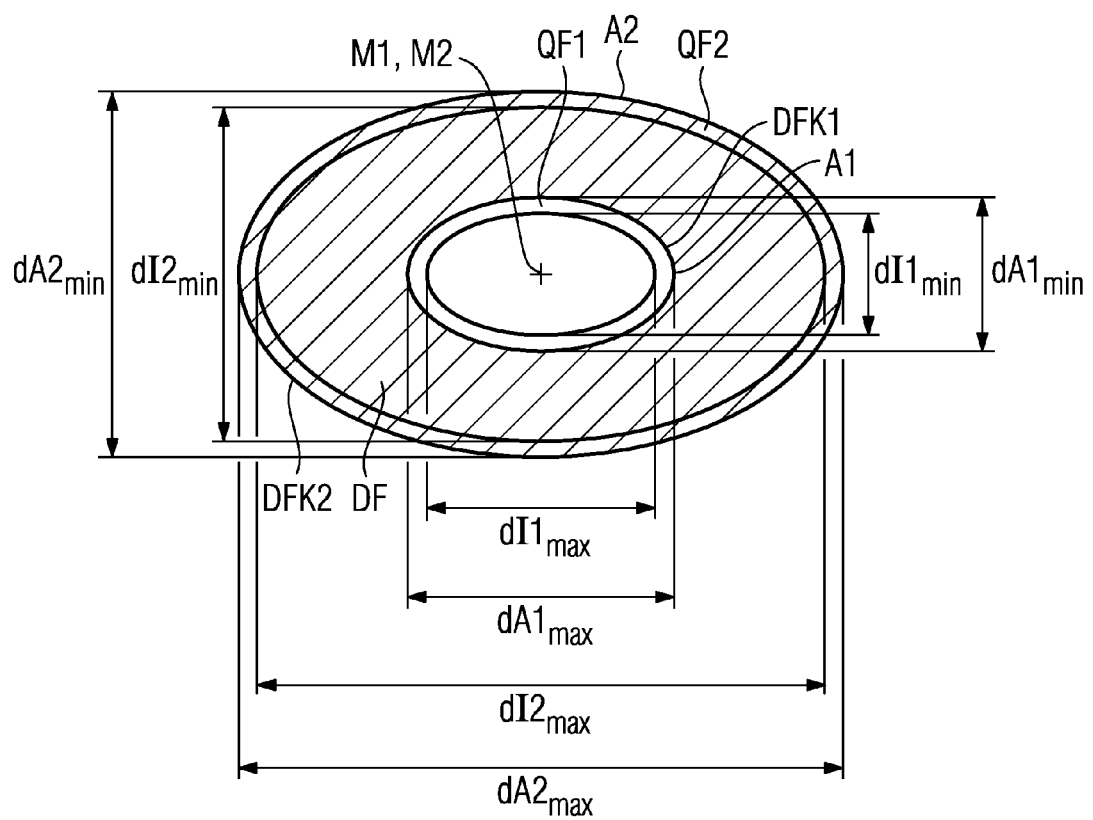
FIG. 6 shows an illustration of the cross-sectional plane 43 in FIG. 5.

As mentioned previously, respectively the minimum and the maximum diameter of the inner wall I1, I2 and respectively the minimum and the maximum diameter of the outer wall A1, A2 are established in an automated fashion in these cross-sectional planes. In the present case, the cross-sectional planes 41 to 45 are relevant for measuring the aneurysm AN, more particularly for establishing the growth or the increase in size of the aneurysm AN. FIG. 6 shows, in an exemplary and simplified fashion, the measurement in the cross-sectional plane 43, in which the minimum diameter $dI1_{min}$ of the inner wall I1, the maximum diameter $dI1_{max}$ of the inner wall I1, the minimum diameter $dA1_{min}$ of the outer wall A1, the maximum diameter $dA1_{max}$ of the outer wall A1, the minimum diameter $dI2_{min}$ of the inner wall I2, the maximum diameter $dI2_{max}$ of the inner wall I2, the minimum diameter $dA2_{min}$ of the outer wall A2, and the maximum diameter $dA2_{max}$ of the outer wall A2 are determined. The diameters in the other cross-sectional planes are established in a corresponding fashion.

On the basis of the values for the diameters established in the cross-sectional planes, the following differences are formed in each cross-sectional plane in the case of the present example embodiment of the invention:

$dI2_{min} - dI1_{min}$ $dI2_{max} - dI1_{max}$ $dA2_{min} - dA1_{min}$ $dA2_{max} - dA1_{max}$ The changes in the minimum diameter of the inner wall $\Delta dI_{min}$, the maximum diameter of the inner wall $\Delta dI_{max}$, the minimum diameter of the outer wall $\Delta dA_{min}$, and the maximum diameter of the outer wall $\Delta dA_{max}$ established from this are visualized in a step 27, for example with reference to the resulting midline or the midlines M1, M2, as shown in FIG. 5.

Alternatively, or in addition thereto, the change in the cross-sectional area ΔQF (ΔQF=QF2−QF1) of the aorta in the respective cross-sectional plane can also be calculated in each case on the basis of the changes in the minimum and maximum diameters of the inner and outer wall of the aorta in a cross-sectional plane and the changes in the cross-sectional area along the resulting midline or along the midlines M1, M2 can be visualized as curves relating to the resulting midline or the midlines. Qualitatively, this would result in a curve profile as visualized in FIG. 5 for the changes in the diameters. When calculating the cross-sectional area, use can be made of equations for circles or equations for ellipses in simple cases, depending on the shape of the cross section of the aorta. Although the inner and outer wall of an aorta usually have an almost circular cross section, the cross section of the inner or outer wall of the aorta may however be described more precisely by a polygonal line. Hence, polygonal lines can also be used for a more precise or more accurate calculation of the cross-sectional areas.

Alternatively, or in addition thereto, at least one difference surface relating to the outer wall A1, A2 of the aorta and/or the inner wall I1, I2 of said aorta, and also the outer contour and/or inner contour of the respective difference surface, can be established in step 26 on the basis of the changes in the minimum and maximum diameters of the inner and outer wall of the aorta A in the direction of the midlines M1, M2, particularly in the region of the aneurysm AN in each cross-sectional plane. The difference surface and the outer and inner contour may again be calculated using e.g. equations for circles, equations for ellipses or polygonal lines. In the case of the present exemplary embodiment of the invention, the procedure is visualized in FIG. 6 on the basis of the cross-sectional plane 43 for the outer wall A1, A2 of the aorta A. If the outer wall A1 in the first volume data record is compared to the outer wall A2 in the second volume data record, FIG. 6 shows that the outer wall of the aorta A has expanded significantly, with this resulting in a difference surface DF, which is shaded in FIG. 6. The difference surface DF relating to the outer wall has an inner contour DFK1 and an outer contour DFK2. Difference surfaces, which have an inner and an outer contour and are comparable to the difference surface DF, which in turn relates to the outer wall of the aorta A and is shown in FIG. 6, can also be determined in the other cross-sectional planes in the region of the aneurysm AN. When seen in the direction of the midlines M1, M2, the totality of the outer contours and the inner contours result in an outer contour surface relating to the outer wall of the aorta and an inner contour surface relating to the outer wall of the aorta.

In the case of the present example embodiment of the invention, a texture is imaged or mapped onto the outer contour surface in step 27. Using different colors, the texture visualizes the differently pronounced changes in the tubular tissue structure in the region of the aneurysm AN on the basis of the previously established changes in the tubular tissue structure in the region of the aneurysm AN. The outer contour surface is superimposed together with the texture as an image element on the first or the second volume data record of the aorta.

Figure 7:
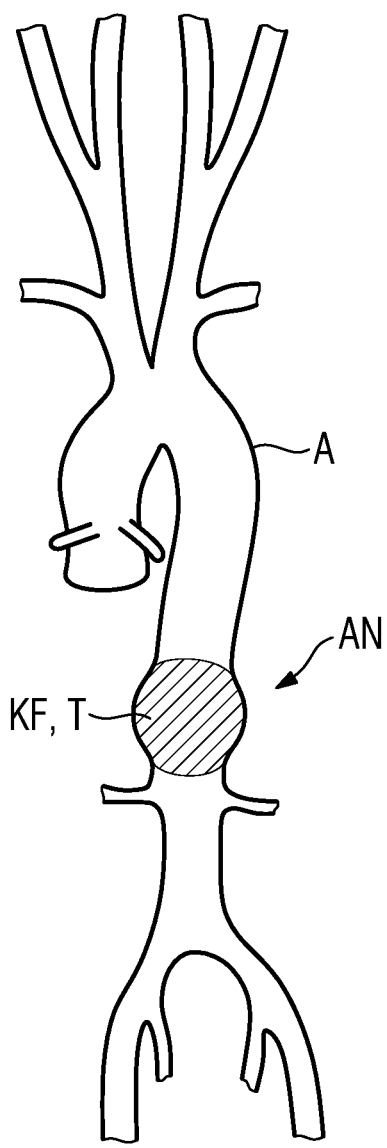
FIG. 7 shows the superimposition of an outer contour surface, overlaid by a texture, on the first volume data record of the aorta.

FIG. 7 schematically shows the superimposition of the outer contour surface KF and the texture T in the first volume data record of the aorta. The superimposition or the visualization of the outer contour surface KF and the texture T can for example be carried out as per the method described in the German patent application DE 10 2009 052 315.4, which does not have a prior publication date, the entire contents of which is hereby incorporated herein by reference.

The visualization of the changes using the texture is preferably color coded such that strong changes are for example illustrated in red, medium severe changes are illustrated in yellow and minor changes are illustrated in green.

Alternatively, or in addition thereto, it is also possible to visualize the inner contour surface, belonging to the outer wall, using an appropriate texture. Similarly, it is also possible to establish an outer contour surface relating to the inner wall I1, I2 and/or an inner contour surface relating to the inner wall I1, I2, and these can be visualized together with a texture.

Accordingly, the method according to an embodiment of the invention can be used to establish changes in the aorta, more particularly changes in an aneurysm in the aorta, and to visualize these to an examiner establishing the findings, on the basis of two volume data records of the aorta generated at different times. This is particularly advantageous if there is not only one aneurysm or not only one anomaly in the aorta, but if there are a number of anomalies to be examined. Using one of the two volume data records, the locations to be diagnosed can be visualized for the examiner establishing the findings, and so the examiner establishing the findings only has to evaluate the data already available for these locations in order to reach a diagnosis.

Unlike the described example embodiment of the invention, it is also possible to examine other tubular tissue structures than the aorta in respect of anomalies, for example the coronary arteries.

Unlike the description above, it is not mandatory either to use the minimum diameter of the inner wall, the maximum diameter of the inner wall, the minimum diameter of the outer wall and the maximum diameter of the outer wall within the scope of the method. Rather, it is possible to establish only one of these diameters, or else it is possible to establish two or three of these diameters, and use them for the visualization.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for establishing at least one change in a tubular tissue structure in a living being from a first time to a second time, which differs from the first, the method comprising:

determining a midline of the tubular tissue structure in a provided first volume data record, generated at the first time, of the tubular tissue structure in the living being, and determining a midline of the tubular tissue structure in a provided second volume data record, generated at the second time, of said tubular tissue structure;

respectively determining at least one of an inner wall of the tubular tissue structure and an outer wall of said tubular tissue structure in the first volume data record of the tubular tissue structure and in the second volume data record of said tubular tissue structure;

registering the tubular tissue structure in the first volume data record and the tubular tissue structure in the second volume data record with respect to one another on the basis of their respective midlines;

respectively establishing at least one of a minimum and a maximum diameter of at least one of the inner wall and the outer wall of said tubular tissue structure, along the midline of the tubular tissue structure in the first volume data record and along the midline of the tubular tissue structure in the second volume data record; and establishing at least one change in at least one of the minimum and the maximum diameter of at least one of the inner wall and the outer wall of said tubular tissue structure, in order to establish the at least one change in the tubular tissue structure along the tubular tissue structure at mutually corresponding positions of the midlines of the tubular tissue structure in the first volume data record and the tubular tissue structure in the second volume data record.

2. The method as claimed in claim 1, wherein the at least one change in the tubular tissue structure, which change occurred from the first to the second time, is visualized.

3. The method as claimed in claim 1, wherein the at least one change in at least one of the minimum and the maximum diameter of at least one of the inner wall and the outer wall of said tubular tissue structure is visualized.

4. The method as claimed in claim 1, wherein the change in the cross-sectional area of the tubular tissue structure is calculated and visualized on the basis of the established at least one change in at least one of the minimum and the maximum at least one of the inner diameter and outer diameter of the tubular tissue structure in the cross-sectional plane of the tubular tissue structure belonging to the at least one change.

5. The method as claimed in claim 1, wherein at least one difference surface, relating to at least one of the outer wall and the inner wall of said tubular tissue structure, and at least one of the outer contour and inner contour, which belong to the difference surface, are established on the basis of the established at least one change in at least one of the minimum and the maximum at least one of the inner diameter and outer diameter of the tubular tissue structure (A) in the cross-sectional plane of the tubular tissue structure belonging to the at least one change.

6. The method as claimed in claim 1, wherein at least one difference surface, relating to at least one of the outer wall and the inner wall of said tubular tissue structure, and at least one of the outer contour and inner contour of the respective difference surface are established for each cross-sectional plane comprising a change, with this being based on established changes in at least one of the minimum and the maximum at least one of the inner diameter and outer diameter of the tubular tissue structure in successive cross-sectional planes of the tubular tissue structure in the direction of the midlines, which cross-sectional planes belong to the changes.

7. The method as claimed in claim 6, wherein the outer contours of successive difference surfaces form an outer contour surface and the inner contours of successive difference surfaces form an inner contour surface, wherein a texture is imaged on at least one of the outer contour surface and the inner contour surface, which texture visualizes the degree of the change at various locations on at least one of the outer contour surface and the inner contour surface.

8. The method as claimed in claim 7, wherein different degrees of the change are visualized using different colors.

9. The method as claimed in claim 1, wherein the tubular tissue structure has at least one blood-carrying vessel.

10. The method as claimed in claim 9, wherein the at least one blood-carrying vessel is the aorta of a human.

11. The method as claimed in claim 9, wherein the at least one change in the at least one bloody-carrying vessel to be established is the change in an aneurysm of the blood-carrying vessel.

12. A calculation unit comprising: a non-transitory storage medium including a calculation program, when executed on the calculation unit, cause the calculation unit to implement the method as claimed in claim 1.

13. A non-transitory data storage medium, comprising a calculation program, to implement the method as claimed in claim 1, stored on the data storage medium and loadable from the data storage medium by a calculation unit in order to carry out a method as claimed in claim 1 once the calculation program has been loaded into the calculation unit.

14. The method as claimed in claim 2, wherein the at least one change in at least one of the minimum and the maximum diameter of at least one of the inner wall and the outer wall of said tubular tissue structure is visualized.

15. The method as claimed in claim 2, wherein the change in the cross-sectional area of the tubular tissue structure is calculated and visualized on the basis of the established at least one change in at least one of the minimum and the maximum at least one of the inner diameter and outer diameter of the tubular tissue structure in the cross-sectional plane of the tubular tissue structure belonging to the at least one change.

16. The method as claimed in claim 2, wherein at least one difference surface, relating to at least one of the outer wall and the inner wall of said tubular tissue structure, and at least one of the outer contour and inner contour, which belong to the difference surface, are established on the basis of the established at least one change in at least one of the minimum and the maximum at least one of the inner diameter and outer diameter of the tubular tissue structure (A) in the cross-sectional plane of the tubular tissue structure belonging to the at least one change.

17. The method as claimed in claim 10, wherein the at least one change in the at least one bloody-carrying vessel to be established is the change in an aneurysm of the blood-carrying vessel.

18. A non-transitory computer readable medium including computer executable instructions that, when executed on a computer device, cause the computer device to implement the method of claim 1.

* * * * *